United States Patent
Reichelt et al.

(10) Patent No.: US 9,260,614 B2
(45) Date of Patent: Feb. 16, 2016

(54) USE OF ARYL OR HETEROARYL SUBSTITUTED DITHIOLENE METAL COMPLEXES AS IR ABSORBERS

(75) Inventors: Helmut Reichelt, Neustadt (DE); Thomas Gessner, Heidelberg (DE); Daniel Heizler, Basel (CH); Urs Lehmann, Basel (CH)

(73) Assignee: BASF SE, Ludwigshafen (DE)

( * ) Notice: Subject to any disclaimer, the term of this patent is extended or adjusted under 35 U.S.C. 154(b) by 337 days.

(21) Appl. No.: 13/885,792

(22) PCT Filed: Nov. 23, 2011

(86) PCT No.: PCT/EP2011/070769
§ 371 (c)(1),
(2), (4) Date: May 16, 2013

(87) PCT Pub. No.: WO2012/069518
PCT Pub. Date: May 31, 2012

(65) Prior Publication Data
US 2013/0234427 A1    Sep. 12, 2013

Related U.S. Application Data

(60) Provisional application No. 61/416,750, filed on Nov. 24, 2010.

(30) Foreign Application Priority Data

Nov. 24, 2010 (EP) ..................................... 10192338

(51) Int. Cl.
| | | |
|---|---|---|
| *C09D 11/02* | (2014.01) | |
| *C09D 11/03* | (2014.01) | |
| *C09D 11/50* | (2014.01) | |
| *C07D 233/84* | (2006.01) | |
| *C07D 233/86* | (2006.01) | |
| *C07D 233/96* | (2006.01) | |
| *C07D 401/14* | (2006.01) | |
| *C07D 409/14* | (2006.01) | |
| *C08K 5/56* | (2006.01) | |
| *B42D 15/00* | (2006.01) | |
| *B41M 3/14* | (2006.01) | |
| *B41M 5/26* | (2006.01) | |

(52) U.S. Cl.
CPC .............. *C09D 11/03* (2013.01); *B42D 15/00* (2013.01); *C07D 233/84* (2013.01); *C07D 233/86* (2013.01); *C07D 233/96* (2013.01); *C07D 401/14* (2013.01); *C07D 409/14* (2013.01); *C08K 5/56* (2013.01); *C09D 11/02* (2013.01); *B41M 3/14* (2013.01); *B41M 5/26* (2013.01); *B41M 5/267* (2013.01)

(58) Field of Classification Search
CPC ........ C09D 11/02; C09D 11/03; C09D 11/50; C07D 233/84; C07D 233/86; C07D 233/96; C07D 401/14; C07D 409/14; C08K 5/56; B42D 15/00; B41M 3/14; B41M 5/26; B41M 5/267
USPC .......... 106/31.14, 31.32, 31.49, 31.64, 31.78; 548/105; 427/145; 283/85
See application file for complete search history.

(56) References Cited

U.S. PATENT DOCUMENTS

| | | | | |
|---|---|---|---|---|
| 5,160,171 | A | * | 11/1992 | Gregory et al. ................ 283/91 |
| 5,282,894 | A | | 2/1994 | Albert et al. |
| 7,282,164 | B2 | * | 10/2007 | Hall et al. .................. 106/31.27 |
| 2008/0241492 | A1 | | 10/2008 | Maeder et al. |
| 2010/0021833 | A1 | | 1/2010 | Lehmann et al. |
| 2010/0310787 | A1 | * | 12/2010 | Lehmann et al. ............. 427/517 |
| 2012/0129090 | A1 | * | 5/2012 | Mamak et al. ............. 106/31.13 |
| 2014/0103635 | A1 | * | 4/2014 | Lehmann et al. ............... 283/85 |

FOREIGN PATENT DOCUMENTS

| | | |
|---|---|---|
| JP | 2003 262953 | 9/2003 |
| JP | 2004 045653 | 2/2004 |
| JP | 2005 099755 | 4/2005 |
| JP | 2009-0523870 | 6/2009 |
| WO | WO 2007/082811 A2 | 7/2007 |
| WO | 2007 091094 | 8/2007 |
| WO | 2007 132214 | 11/2007 |
| WO | 2008 086931 | 7/2008 |

OTHER PUBLICATIONS

Aragoni, M. C., et al., "NIR Dyes Based on [M(R,R'Timdt)2} Metal-dithiolenes: Additivity of M, R, and R' Contributions to Tune the NIR Absorption (M=Ni, Pd, Pt: R, R'timdt= Monoreduced Form of Disubstituted Imadazolidine=2,4,5-trithione)," Eur. J. Inorg. Chem., pp. 1939 to 1947, (2003).

Arca, M., et al., Synthesis, X-ray crystal structure and spectrospolyc characterization of the new dithiolene [Pd(Et2timdt)2] and of its adduct with molecular diiodine[Pd(Et2timdt)2] •I2 •ChC13 EEt2timidt = monoanion of 1,3-diethylimidazolidine-2,4,5-trithione), J. Chem. Soc., pp. 3731 to 3736, (1998).

International Search Report Issued Feb. 28, 2012 in PCT/EP11/070769 Filed Nov. 23, 2011.

U.S. Appl. No. 14/115,878, filed Nov. 6, 2013, Lehmann et al.
U.S. Appl. No. 14/238,382, filed Feb. 11, 2014, Suraru et al.

E. Grigiotti et al., Metal-Dithiolenes of Disubstituted Imidazolidine-2, 4,5-trithione Monoanion. An Electrochemical and EPR Study, Portugalie electrochimica Acta 22(2004) pp. 25-41.

* cited by examiner

*Primary Examiner* — Helene Klemanski
(74) *Attorney, Agent, or Firm* — Oblon, McClelland, Maier & Neustadt, L.L.P.

(57) ABSTRACT

The present invention relates to the use of specific metal complexes of dithiolenes with aryl or heteroarylsubstituted imidazolidine-2-chalcogenone-4,5-dithione ligands as colorless IR absorbers.

14 Claims, No Drawings

USE OF ARYL OR HETEROARYL SUBSTITUTED DITHIOLENE METAL COMPLEXES AS IR ABSORBERS

BACKGROUND OF THE INVENTION

The present invention relates to the use of specific metal complexes of dithiolenes with aryl or heteroaryl substituted imidazolidine-2-chalcogenone-4,5-dithione ligands as colourless IR absorbers. The invention also relates to novel dithiolene metal complexes, a printing ink formulation for security printing and security documents.

DESCRIPTION OF THE RELATED ART

Colourless, or at least barely coloured, IR absorbers meet a significant technical need in a wide range of applications, such as security printing (bank notes, credit cards, identity cards, passports etc.), invisible and/or IR readable bar codes, the laser-welding of plastics, the curing of surface-coatings using IR radiators, the drying and curing of print, the fixing of toners on paper or plastics, optical filters for PDPs (plasma display panels), laser marking e.g. of paper or plastics, the heating of plastics preforms, heat shielding applications, etc. A large number of organic and inorganic substances belonging to different compound classes and with a great variety of different structures are known for the application as IR absorbers. Notwithstanding that large numbers of known compound classes and structures, the provision of products with a complex profile of properties often presents difficulties. There is a continuing demand for IR absorber that are "colourlessness" (i.e. with the minimum possible inherent colour), and that simultaneously meet the technical stability requirements (chemical stability, heat stability and/or light stability).

A special field of application for colourless IR absorbers regards inks for printing processes which are used for printing currency and other security documents, also referred to as "security printing". Typical security printing processes are processes, wherein an ink composition is employed that is designed to selectively absorb radiation in parts of the "optical infrared" spectrum, whilst being transparent in other parts of it. IR absorbers for security printing are available, for example, from "American Dye Source", but virtually all of them have a noticeable absorption in the VIS range of the spectrum (from 400 to 700 nm).

US 2008/0241492 describes an intaglio printing ink for a security printing process, wherein the ink comprises a polymeric organic binder and an infrared absorbing material that comprises transition element atoms or ions whose infrared absorption is a consequence of electronic transitions within the d-shell of the transition element. Suitable transition elements are Ti, V, Cr, Mn, Fe, Co, Ni, and Cu. In a suitable embodiment, the infrared absorbing material is a glass, in which there is a coordination of the transition element ions to phosphate and/or fluoride anions present in the glass. In a further suitable embodiment, the infrared absorbing material is an IR-absorbing transition element atom or ion bound to the polymer binder of the ink. In particular, the infrared absorbing material is an IR-absorbing complex of a transition element atom or ion and a binding site contained in the polymer, e.g. an organic thiourea-copper(II) complex dissolved in the polymeric binder.

U.S. Pat. No. 5,282,894 describes a liquid useful as printing ink that contains one or more dyes with their absorption maximum within the range from 700 to 1200 nm selected from phthalocyanines, naphthalocyanines, nickel-dithiolene complexes, aminium compounds of aromatic amines, methine dyes or azulenesquaric acid dyes, as well as solvent and binder.

WO 2007/091094 describes an image article that comprises a substrate having a security image coated on at least a portion thereof, wherein the security image comprises a defined infrared-absorbing compound, for example Pigment Green 8, that does not create a strongly coloured security image. The disclosed infrared-absorbing compounds still have a noticeable absorption in the VIS range of the spectrum.

WO 2007/132214 describes a composition comprising an ink and an infrared-absorbing material that comprises a metal, a metal salt, a metal oxide or metal nitride, wherein the metal is in particular selected from periods 4, 5 or the lanthanides. Also described is an article comprising a substrate having imaged thereon an infrared-absorbing material to form a security image, and a method of manufacture of such an article by image-wise application of a composition comprising such an infrared-absorbing material to a substrate.

M. Arca et al. describe in J. Chem. Soc., Dalton Trans. 1998, 3731-3736 metal dithiolenes (see scheme 1) belonging to the general class $[M(R,R'timdt)_2]$ (M=Ni, Pd; (R,R'timdt)=monoanion of disubstituted imidazolidine-2,4,5-trithione; R and R'=ethyl or isopropyl). As those metal dithiolenes exhibit large $\pi$ delocalization they can also be characterized by the aromatic resonance structure on the right:

Scheme 1

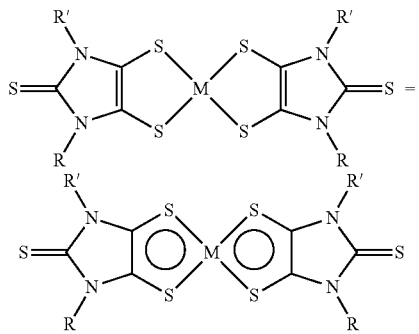

JP 2003-262953 A, JP2004-045653 A and JP 2005-99755 A describe metal dithiolenes [M(R,R'timdt)2], wherein R and R' are selected from unsubstituted and substituted alkyl, cycloalkyl and aryl groups.

M. C. Aragoni et al. describe in Eur. J. Inorg. Chem. 2003, 1939-1947 NIR dyes based on $[M(R,R'timdt)_2]$ metal dithiolenes, wherein R and R' are inter alia selected from unsubstituted and substituted aryl groups.

WO 2008/086931 teaches the use of dithiolene metal complexes [M(L)2], wherein L is the monoanion of a disubstituted imidazolidine-2-chalcogenone-4,5-dithione and the chalcogene is O or S, as colourless IR absorbers. Whereas aryl substituted compounds are mentioned in very general terms, there is no concrete teaching with regard to those compounds. In particular, in all examples the nitrogen atoms bear only unsubstituted and substituted alkyl and alkenyl groups. Especially in respect of colourlessness, the compounds described in WO 2008/086931 are superior to the IR absorbers known before, while simultaneously meeting other technical requirements, such as good fastness to light or good heat stability when incorporated into plastics material (e.g. for laser-welding). Nevertheless, for high-end applications the dithiolene metal complexes described in WO 2008/

086931 are still in need of improvement with regard to their fastness properties, e.g. fastness to chemicals and boiling water. Those properties are important in particular for applications in the field of security printing.

It has now been found, surprisingly, that dithiolene metal complexes [M(L)2], wherein L is selected from monoanions of a disubstituted imidazolidine-2-chalcogenone-4,5-dithione and the chalcogene is O or S, with N-aryl substituents or N-heteroaryl substituents instead of N-alkyl substituents, exhibit high resistance against chemicals and solvents without loosing their other advantages like colourlessness, good light stability and good thermal stability. They can be advantageously employed as IR absorbers for security printing and the laser-welding of plastics. Due to their unique application properties they are in particular suitable as IR absorbers for security printing, especially for bank notes.

SUMMARY OF THE INVENTION

In a first aspect, the invention provides the use of compounds of the general formula (I) as colourless IR absorbers

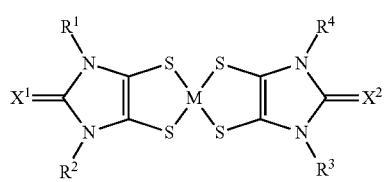
(I)

wherein
M is Ni, Pd, Pt,
$X^1$, and $X^2$ are each independently of each other sulfur or oxygen,
$R^1$, $R^2$, $R^3$, and $R^4$ are independently selected from unsubstituted or substituted aryl and unsubstituted or substituted heteroaryl.

In a further aspect, the invention provides new compounds of the general formula (I)

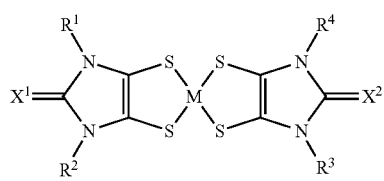
(I)

wherein
M is Ni, Pd, Pt,
$X^1$ is oxygen,
$X^2$ is sulfur or oxygen,
$R^1$, $R^2$, $R^3$, and $R^4$ are independently selected from unsubstituted or substituted aryl and unsubstituted or substituted heteroaryl.

In a further aspect, the invention provides a printing ink formulation for security printing, comprising at least one compound of the general formula (I) as defined above and in the following.

In a further aspect, the invention provides a security document, comprising a substrate and at least one compound of the general formula (I) as defined above and in the following.

In a further aspect, the invention provides a security document, obtainable by a printing process, wherein a printing ink formulation is employed that comprises at least one compound of the general formula (I) as defined above and in the following.

DESCRIPTION OF THE INVENTION

The compounds of the general formula (I) have at least one of the following advantageous properties:
good fastness to chemicals, in particular fastness to bleaching with hypochlorite and fastness to solvents (like toluene, acetone or dichloromethane),
good fastness to boiling water,
good fastness to light,
colourlessness (i.e. minimal absorption in the VIS range of the spectrum (from 400 to 700 nm))
good heat stability,
high compatibility with a multiplicity of formulations, in particular printing ink formulations used in security printing and thermoplastic polymer formulations used for laser-welding.

For definition and description of fastness requirements in banknote printing see e.g. "Chemical and Physical Resistance" in "Extract of the ANNEX 13 of the Technical Specification for Euro banknote production" (European Central Bank; July 2004).

The compounds of general formula (I) can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastics preforms, and for heat shielding applications.

Preferably, in the compounds of the general formula (I) M is Ni, Pd or Pt.

In particular, in the compounds of the general formula (I) M is Ni.

In the context of the invention, the expression "halogen" denotes in each case fluorine, bromine, chlorine or iodine, preferably fluorine, chlorine or bromine, in particular fluorine or chlorine.

In the context of the present invention, the expression "alkyl" comprises straight-chain or branched alkyl groups. Alkyl is preferably $C_1$-$C_{30}$-alkyl, more preferably $C_1$-$C_{20}$-alkyl, most preferably $C_1$-$C_{12}$-alkyl, in particular $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression alkyl also comprises alkyl radicals whose carbon chains may be interrupted by one or more groups which are independently selected from —O— and —S—.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^1E^2$ where $E^1$, and $E^2$ are each independently hydrogen, alkyl, cycloalkyl, heterocycloalkyl, aryl or heteroaryl. Cycloalkyl, heterocycloalkyl, aryl and heteroaryl substituents of the alkyl groups may in turn be unsubstituted or substituted; suitable substituents are the substituents mentioned below for these groups.

The expression substituted alkyl group also comprises alkyl radicals that have one or more (e.g. 1, 2, 3, 4, 5 or more than 5) substituents and whose carbon chains may be interrupted by one or more groups which are independently selected from —O— and —S—.

Carboxylate and sulfonate respectively represent a metal carboxylate or metal sulfonate, or a carboxylic ester function or sulfonic ester function.

The above remarks regarding alkyl also apply to the alkyl moiety in alkoxy, alkylthio (=alkylsulfanyl), monoalkylamino and dialkylamino.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each independently hydrogen, alkyl, cycloalkyl, heterocycloalkyl, aryl or heteroaryl. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-,3- and 4-methylcyclohexyl, 2-,3- and 4-ethylcyclohexyl, 2-,3- and 4-propylcyclohexyl, 2-,3- and 4-isopropylcyclohexyl, 2-,3- and 4-butylcyclohexyl, 2-,3- and 4-sec.-butylcyclohexyl, 2-,3- and 4-tert-butylcyclohexyl, 2-,3- and 4-methylcycloheptyl, 2-,3- and 4-ethylcycloheptyl, 2-,3- and 4-propylcycloheptyl, 2-,3- and 4-isopropylcycloheptyl, 2-,3- and 4-butylcycloheptyl, 2-, 3- and 4-sec-butylcycloheptyl, 2-,3- and 4-tert-butylcycloheptyl, 2-,3-,4- and 5-methyl-cyclooctyl, 2-,3-,4- and 5-ethylcyclooctyl, 2-,3-,4- and 5-propylcyclooctyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —$NR^a$—, —C(=O)—, —S(=O)— and/or —$S(=O)_2$—. $R^a$ is preferably hydrogen, alkyl, cycloalkyl, heterocycloalkyl, aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, amidino, $NE^5E^6$ where $E^5$ and $E^6$ are each independently hydrogen, alkyl, cycloalkyl, heterocycloalkyl, aryl or heteroaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkylthio (=heterocycloalkylsulfanyl), (monoheterocycloalkyl)amino and (diheterocycloalkyl)amino.

In the context of the present invention, the term "aryl" refers to mono- or polycyclic aromatic hydrocarbon radicals. Suitable and preferred unsubstituted and substituted aryl groups are defined in the following with regard to the substituents $R^1$, $R^2$, $R^3$, and $R^4$.

In the context of the present invention, the term "heteroaryl" (hetaryl) refers to unsubstituted or substituted heteroaromatic, mono- or polycyclic groups. Suitable and preferred unsubstituted and substituted heteroaryl groups are defined in the following with regard to the substituents $R^1$, $R^2$, $R^3$, and $R^4$.

According to the invention, $R^1$, $R^2$, $R^3$, and $R^4$ are independently selected from unsubstituted or substituted aryl and unsubstituted or substituted heteroaryl.

The unsubstituted or substituted aryl groups $R^1$, $R^2$, $R^3$, and $R^4$ are independently selected from unsubstituted or substituted mono- or polycyclic aromatic hydrocarbon radicals, preferably having 6 to 24 carbon atoms, more preferably having 6 to 20 carbon atoms, especially having 6 to 14 carbon atoms as ring members.

The unsubstituted or substituted aryl groups $R^1$, $R^2$, $R^3$, and $R^4$ are preferably selected from unsubstituted or substituted phenyl, unsubstituted or substituted naphthyl, unsubstituted or substituted indenyl, unsubstituted or substituted fluorenyl, unsubstituted or substituted anthracenyl, unsubstituted or substituted phenanthrenyl, unsubstituted or substituted naphthacenyl, unsubstituted or substituted chrysenyl, unsubstituted or substituted pyrenyl, unsubstituted or substituted coronenyl and unsubstituted or substituted perylenyl.

The unsubstituted or substituted aryl groups $R^1$, $R^2$, $R^3$, and $R^4$ are more preferably selected from unsubstituted or substituted phenyl and unsubstituted or substituted naphthyl.

The unsubstituted or substituted aryl groups $R^1$, $R^2$, $R^3$, and $R^4$ are in particular selected from unsubstituted or substituted phenyl.

In a preferred embodiment, at least one of groups $R^1$, $R^2$, $R^3$, and $R^4$ is unsubstituted phenyl. In a particular preferred embodiment, all of groups $R^1$, $R^2$, $R^3$, and $R^4$ are unsubstituted phenyl.

The substituted aryl groups $R^1$, $R^2$, $R^3$, and $R^4$ may, depending on the number and size of their ring systems, have one or more (e.g. 1, 2, 3, 4, 5 or more than 5) substituents. The substituents of the substituted aryl groups $R^1$, $R^2$, $R^3$, and $R^4$ are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^1E^2$ where $E^1$ and $E^2$ are each independently hydrogen, alkyl, cycloalkyl, heterocycloalkyl, aryl or heteroaryl. The alkyl, alkoxy, alkylamino, alkylthio, cycloalkyl, heterocycloalkyl, aryl and heteroaryl substituents on the substituted aryl groups $R^1$, $R^2$, $R^3$, and $R^4$ may in turn be unsubstituted or substituted. Reference is made to the substituents mentioned for these groups above and in the following.

The substituents on the substituted aryl groups $R^1$, $R^2$, $R^3$, and $R^4$ are preferably selected from alkyl; alkoxy; alkyl or alkoxy whose carbon chain is interrupted by one or more nonadjacent groups selected from —O—, —S—, —$NR^a$—, —C(=O)—, —S(=O)— and/or —S(=O)$_2$—, wherein $R^a$ is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted aryl groups $R^1$, $R^2$, $R^3$, and $R^4$ are preferably substituted phenyl which bears 1, 2, 3, 4 or 5 substituents. The substituted aryl groups $R^1$, $R^2$, $R^3$, and $R^4$ are more preferably substituted phenyl which bears preferably 1, 2 or 3 substituents.

The substituted aryl groups $R^1$, $R^2$, $R^3$, and $R^4$ are preferably selected from aryl groups substituted by at least one alkyl group ("alkaryl", also referred to as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents on the alkaryl groups may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents. The alkyl substituents on the alkaryl groups $R^1$, $R^2$, $R^3$, and $R^4$ are preferably selected from $C_1$-$C_{20}$-alkyl, more preferably $C_1$-$C_{12}$-alkyl and most preferably $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The substituted aryl groups $R^1$, $R^2$, $R^3$, and $R^4$ are preferably selected from 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butyl-phenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxy-phenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl, 2-, 3- and 4-fluorophenyl, 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl, (2-fluoro-6-methyl)phenyl, (2-fluoro-6-ethyl)phenyl, (4-fluoro-6-methyl)phenyl, (4-fluoro-6-ethyl)phenyl, pentafluorophenyl, pentachlorophenyl, 2,3,5,6-tetrafluorophenyl, 2,3,5,6-tetrachlorophenyl, 2,4-difluorophenyl, 2,4,5-trifluorophenyl, 2,4,6-trifluorophenyl, 2,5-difluorophenyl, 2-fluoro-S-(trifluoromethyl)phenyl, 2-fluoro-S-methylphenyl, 2,6-difluorophenyl, 4-chloro-2-fluorophenyl, 2,3,4-trifluorophenyl, 2,3,6-trifluorophenyl, 2,3,4,5-tetrafluorophenyl, 2-chloro-6-fluorophenyl, 2-fluoro-4-methylphenyl, 3-chloro-2,4-difluorophenyl, 3,5-dichloro-2,4-difluorophenyl, 1-chloro-4-fluorophenyl, 2-fluoro-3-(trifluoromethyl) phenyl, 2-(trifluoromethyl)-6-fluorophenyl, 2,3,4,6-tetrafluorophenyl, 3-chloro-2-fluorophenyl, 5-chloro-2-fluorophenyl, 2,3,5-trifluorophenyl, 4-(trifluoromethyl)-2,3,5,6-tetrafluorophenyl, 2-chloro-4,6-difluorophenyl, 2,5-difluoro-4-(trifluoromethyl)phenyl, 4-trifluoromethyl-2,3-difluorophenyl, 2,4-difluoro-3-(trifluoromethyl)phenyl, 2-fluoro-4-(trifluoromethyl)phenyl, 2-fluoro-S-methylsulphonylpenyl, 2-fluoro-4-hydroxymethylphenyl, 4-(trifluoromethyl)phenyl, 2-chloro-4-(trifluoromethyl)phenyl, 2,6-dichloro-4-(trifluoromethyl)phenyl, 4-(trifluoromethyl)-2,3,5,6-tetrafluorophenyl, 3-fluoro-4-(trifluoromethyl)phenyl, 2,5-difluoro-4-(trifluoromethyl)phenyl, 3,5-difluoro-4-(trifluoromethyl)phenyl, 2,3-difluoro-4-(trifluoromethyl)phenyl, 2,4-bis(trifluoromethyl)phenyl, 3-chloro-4-(trifluoromethyl) phenyl, 2,4,6-tris(trifluoromethyl)phenyl, 3,4-bis(trifluoromethyl)phenyl, 2-fluoro-3-(trifluoromethyl)phenyl, 2-methyl-4-(trifluoromethyl)phenyl, 3,5-dichloro-4-(trifluoromethyl)phenyl, 2,3,6-trichloro-4-(trifluoromethyl) phenyl, etc.

The unsubstituted or substituted heteroaryl groups $R^1$, $R^2$, $R^3$, and $R^4$ are independently selected from unsubstituted or substituted heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The heteroaryl groups have preferably 5 to 18, e.g. 5, 6, 8, 9, 10, 11, 12, 13 or 14, ring atoms.

Unsubstituted or substituted monocyclic heteroaryl groups $R^1$, $R^2$, $R^3$, and $R^4$ are preferably selected from unsubstituted or substituted 5- or 6-membered heteroaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-S-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-S-yl, 1,3,4-oxadiazol-2-yl, 1,2,4-thiadiazol-3-yl, 1,2,4-thiadiazol-S-yl, 1,3,4-thiadiazol-2-yl, 4H[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Unsubstituted or substituted polycyclic heteroaryl groups $R^1$, $R^2$, $R^3$, and $R^4$ preferably have 2, 3, 4 or more than 4 fused rings. The fused-on rings may be aromatic, saturated or partly unsaturated. Examples of polycyclic heteroaryl groups $R^1$, $R^2$, $R^3$, and $R^4$ are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thio-phenyl, naphtha[2,3-b]furyl, dihydroindolyl, dihydroindolizinyl, dihydroisoindolyl, dihydroquinolinyl and dihydroisoquinolinyl.

The substituted hetaryl groups $R^1$, $R^2$, $R^3$, and $R^4$ may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, heteroaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^3E^4$ where $E^3$ and $E^4$ are each independently hydrogen, alkyl, cycloalkyl, heterocycloalkyl, aryl or heteroaryl. Halogen substituents are preferably fluorine, chlorine or bromine.

The substituents on the substituted hetaryl groups $R^1$, $R^2$, $R^3$, and $R^4$ are preferably selected from alkyl; alkoxy; alkyl or alkoxy whose carbon chain is interrupted by one or more nonadjacent groups selected from —O—, —S—, —$NR^b$—, —C(=O)—, —S(=O)— and/or —S(=O)$_2$—, wherein $R^b$ is hydrogen, alkyl, cycloalkyl, heterocycloalkyl, aryl or heteroaryl; haloalkyl; haloalkoxy; cycloalkyl; fluorine; chlorine; bromine; cyano and nitro.

The substituted hetaryl groups $R^1$, $R^2$, $R^3$, and $R^4$ are preferably selected from heteroaryl groups substituted by at least one alkyl group. Alkyl substituted heteroaryl groups may, depending on the size of the aromatic ring system, have one or more (e.g. 1, 2, 3, 4, 5, 6, 7, 8, 9 or more than 9) alkyl substituents. The alkyl substituents on the heteroaryl groups may be unsubstituted or substituted. In this regard, reference is made to the following statements regarding unsubstituted and substituted alkyl. In a preferred embodiment, the heteroaryl groups have exclusively unsubstituted alkyl substituents. The alkyl substituents on the hetaryl groups $R^1$, $R^2$, $R^3$, and $R^4$ preferably selected from $C_1$-$C_{20}$-alkyl, more preferably $C_1$-$C_{12}$-alkyl and most preferably $C_1$-$C_6$-alkyl. Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The invention also relates to novel compounds of the general formula (I), wherein $X^1$ is oxygen and $X^2$ is sulfur or oxygen.

Those compounds can be obtained from the corresponding sulfur compounds ($X^1$, $X^2$=S) by oxidation in a suitable solvent. Suitable oxidation agents are oxygen and oxygen containing gas mixtures, in particular atmospheric oxygen. Suitable solvents are inert under the oxidation conditions. Preferred solvents are halogenated hydrocarbons, e.g. dichloromethane.

Compounds of the general formula (I), wherein $X^1$ is oxygen and $X^2$ is sulfur or oxygen can also be obtained from disubstituted imidazolidine-2,4,5-triones of the formula (II):

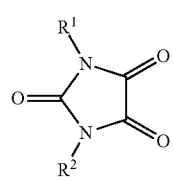

(II)

wherein $R^1$ and $R^2$ have one of the aforementioned meanings. Suitable methods are described in WO 2008/086931 which is incorporated herein by reference.

Of particular interest are the following compounds (1) to (36):

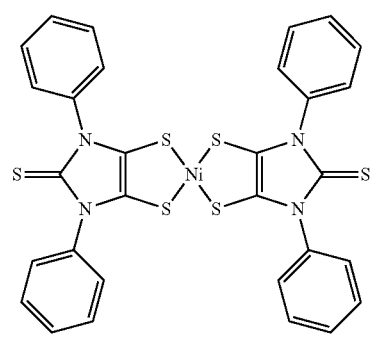

(1)

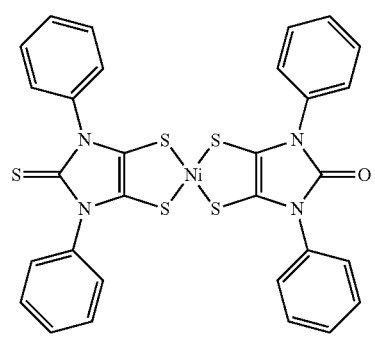

(2)

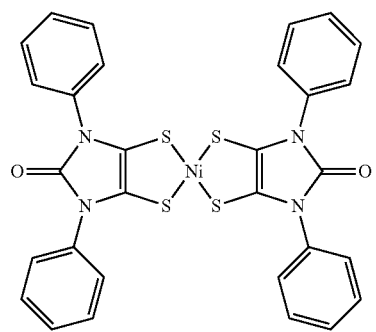

(3)

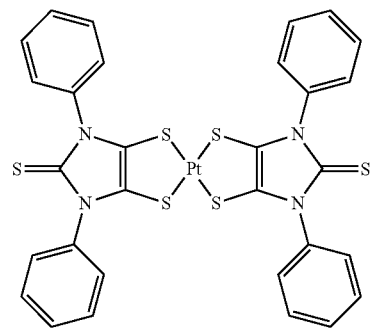

(4)

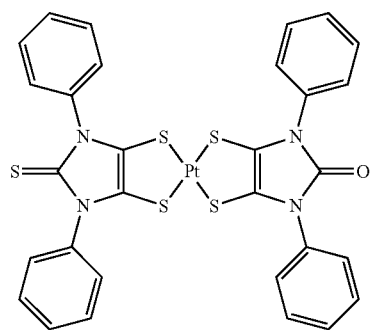
(5)
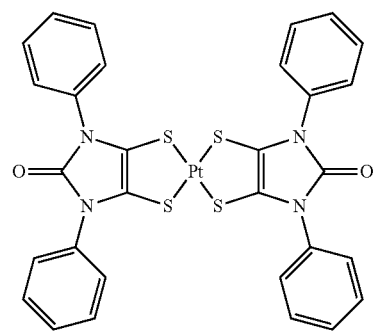
(6)
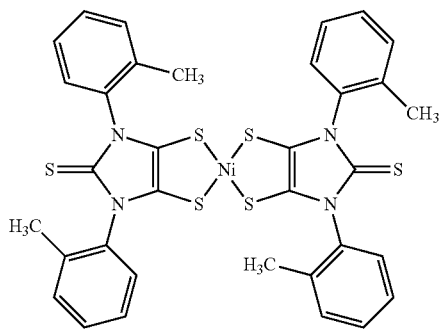
(7)
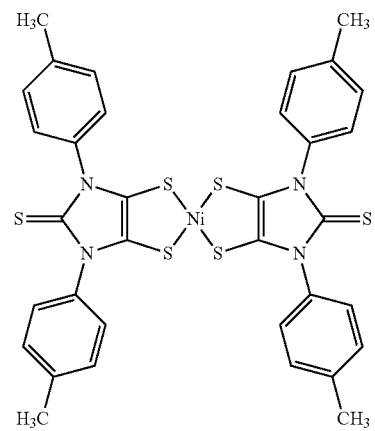
(8)
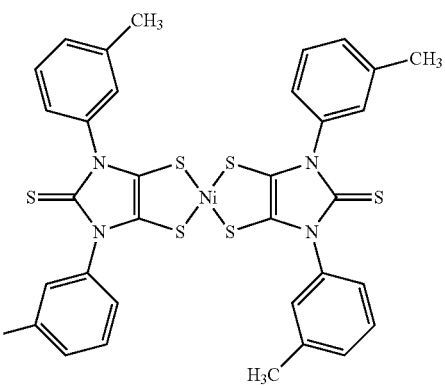
(9)
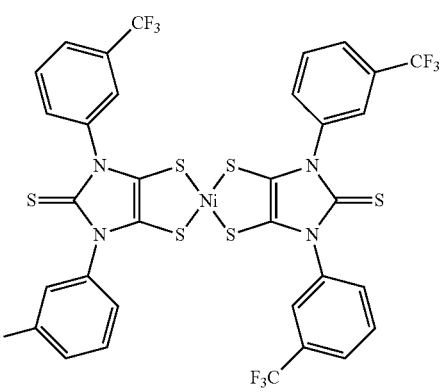
(10)
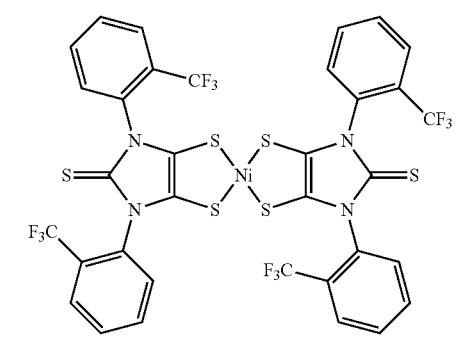
(11)
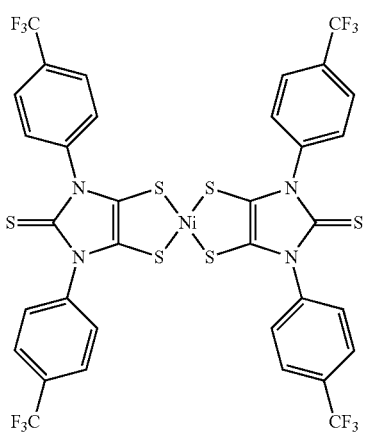
(12)

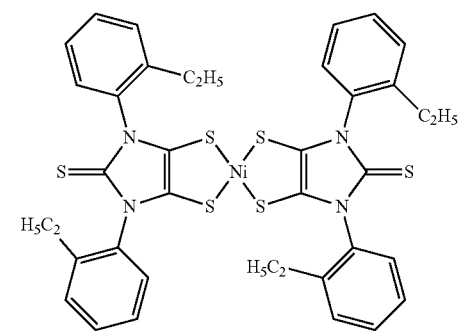
(13)
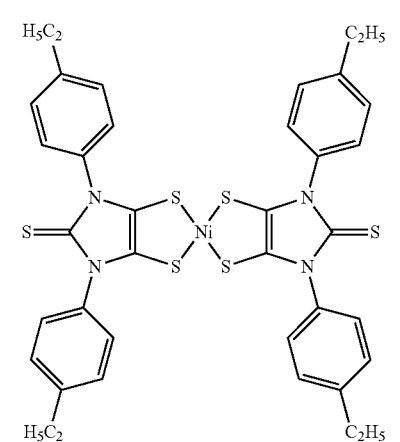
(14)
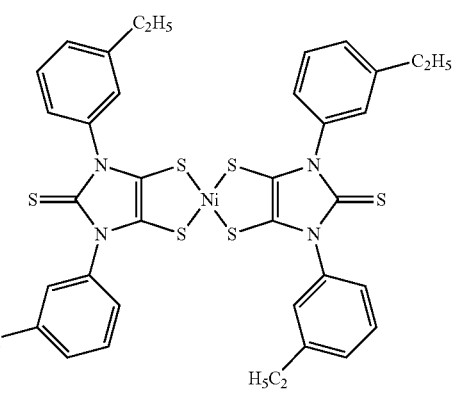
(15)
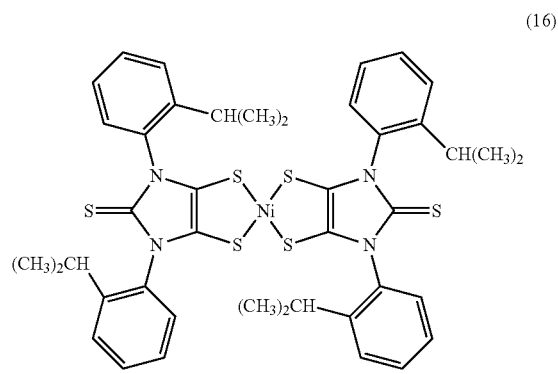
(16)
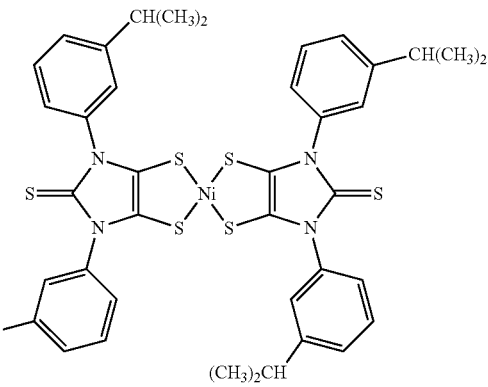
(17)
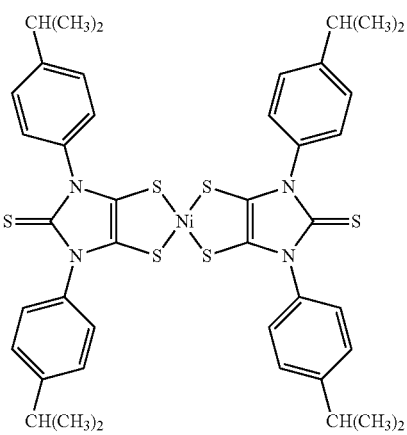
(18)
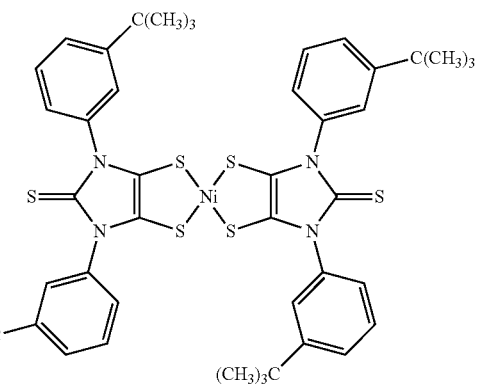
(19)

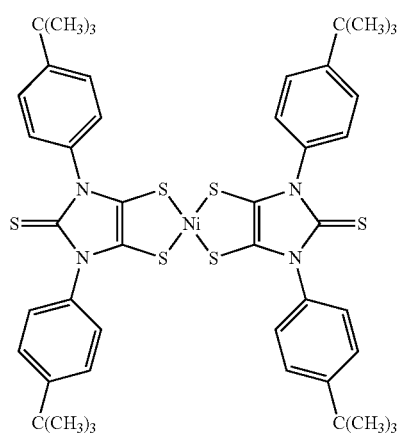
(20)
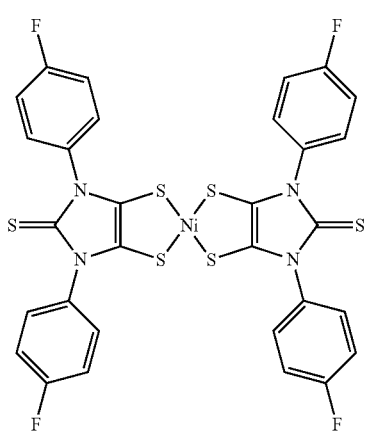
(21)
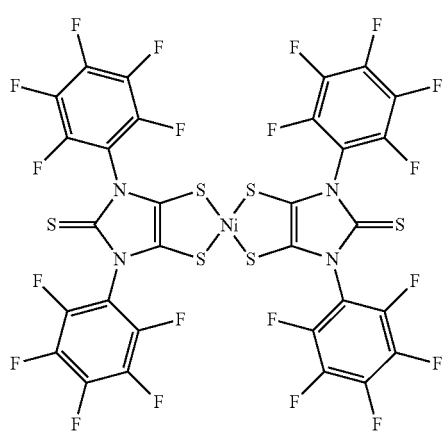
(22)
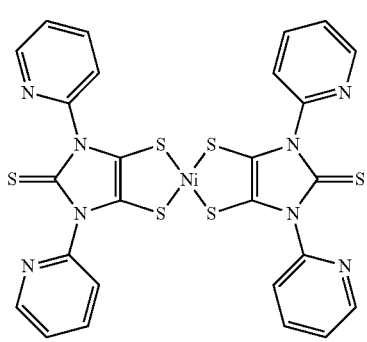
(23)
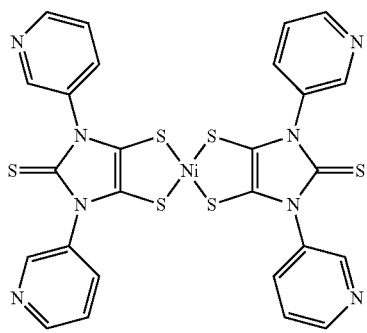
(24)
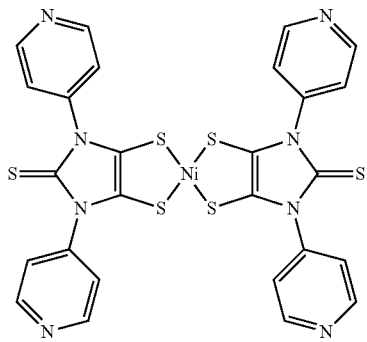
(25)
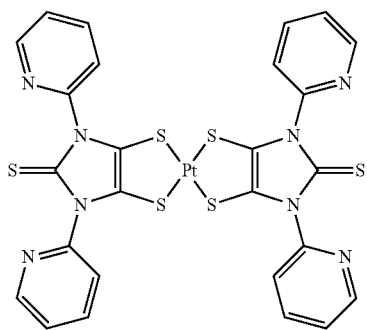
(26)
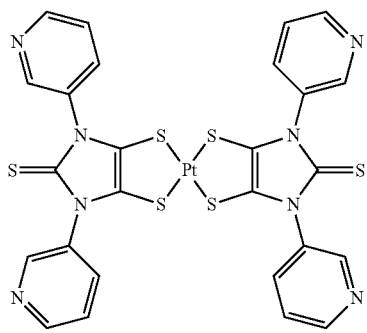
(27)

(28)
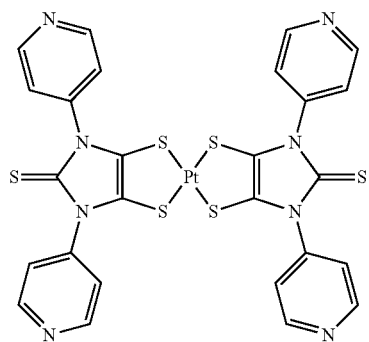
(29)
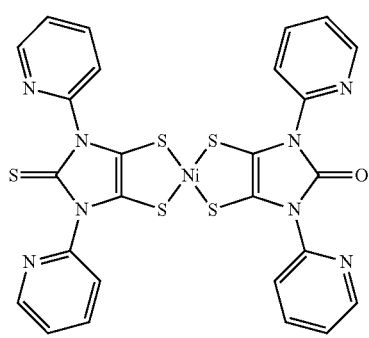
(30)
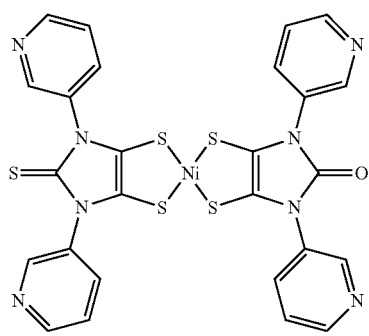
(31)
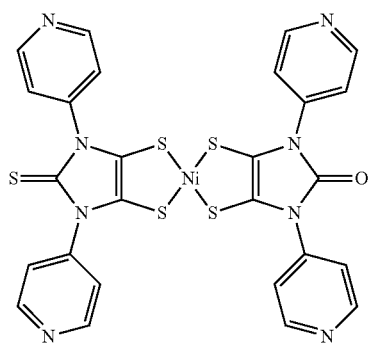
(32)
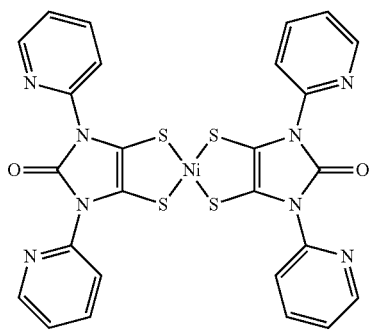
(33)
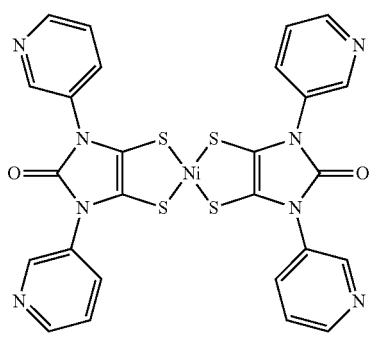
(34)
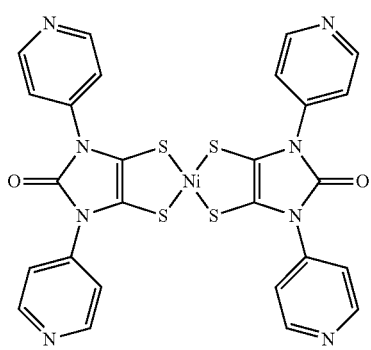
(35)
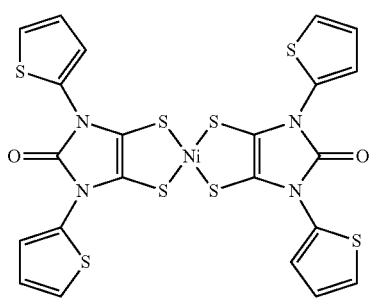
(36)
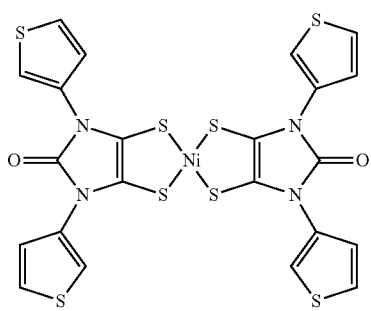

(37)

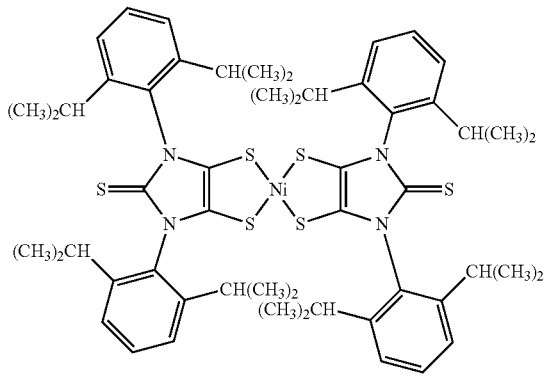

The IR absorbers of formula (I) can also be used in the form of a mixture, comprising at least one compound of the general formula (I) and at least one further IR absorber different from compounds of the general formula (I). Suitable further IR absorbers are in principle all known classes of IR absorbers that are compatible with the compounds of the general formula (I). Preferred further IR absorbers are selected from polymethines, phthalocyanines, naphthalocyanines, quinone-diimmonium salts, aminium salts, rylenes, inorganic IR absorbers and mixtures thereof. Further polymethine IR absorbers are preferably selected from cyanines, squaraines, croconaines and mixtures thereof. Further inorganic IR absorbers are preferably selected from indium tin oxide, antimony tin oxide, lanthanum hexaboride, tungsten bronzes, copper salts etc.

The IR absorbers can be generally used in a concentration of from 10 ppm to 25%, preferably 100 ppm to 10%, depending on the chosen application.

The afore-mentioned IR absorbers of the general formula (I) and IR absorber mixtures are especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, IR-absorption plays an important role. Most of the actually circulating currency carries not only visibly coloured printings, but also specific features which are only detectable in the infrared part of the spectrum. Generally, these IR-features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. It has now been found that the compounds of the general formula (I) because of their unique application properties are especially suitable for printing ink formulations that are employed for security printing and in particular for bank notes.

In security printing, the IR absorber is added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

In the context of the present invention, the expression "printing ink" also encompasses formulations that in addition to at least one IR absorber of the general formula (I) comprise a colorant. The expression "printing ink" also encompasses printing lacquers that comprise no colorant.

The printing ink formulation for security printing according to the invention preferably comprises
a) at least one compound of the general formula (I) as defined above,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"—Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compounds of the general formula (I) are present in the printing ink formulation in dissolved form or in solid form (in a finely divided state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, and metal complex pigments. Also suitable are synthetic white pigments with air inclusions to increase the light scattering, such as the Rhopaque® dispersions.

Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one compound of the general formula (I),
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the IR absorber (I) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The afore-mentioned IR absorbers of the general formula (I) and IR absorber mixtures are also especially suitable for laser welding of plastics.

The laser welding is preferably carried out using an ND:YAG laser at 1064 nm or using a diode laser at 980 nm or 940 nm. The concentration of the IR absorber of the general formula (I) or an IR absorber mixtures is e.g. from 5 to 500 ppm, preferably from 10 to 200 ppm.

In laser welding, plastics components are welded to one another. The plastics components to be fused may have any shape. For example, at least one of the plastics components may be a film.

The dithiolenes (I) used according to the invention are suitable for welding transparent at least translucent plastics materials. The employed plastics materials may be colourless or coloured. In principle, the plastics components to be fused may be composed of the same polymer or of different polymers. Preferably, the plastics components employed for laser welding are selected from thermoplastic polymers. However, it is also possible that neither of the plastics components to be fused is composed of thermoplastic; however, a coating of at least one part with a thermoplastic comprising at least one compound of the general formula (I) is required.

The plastics components employed for laser welding preferably comprise or consist of at least one polymer selected from polyolefins, polyolefin copolymers, polytetrafluoroethylenes, ethylene-tetrafluoroethylene copolymers, polyvinyl chlorides, polyvinylidene chlorides, polyvinyl alcohols, polyvinyl esters, polyvinyl alkanals, polyvinyl ketals, polyamides, polyimides, polycarbonates, polycarbonate blends, polyesters, polyester blends, poly(meth)acrylates, poly(meth)acrylate-styrene copolymer blends, poly(meth)acrylate-polyvinylidene difluoride blends, polyurethanes, polystyrenes, styrene copolymers, polyethers, polyether ketones and polysulfones and mixtures thereof.

Preference is given to matrix polymers from the group of the polyolefins, polyolefin copolymers, polyvinyl alkanals, polyamides, polycarbonates, polycarbonate-polyester blends, polycarbonate-styrene copolymer blends, polyesters, polyester blends, poly(meth)acrylates, poly(meth)acrylate-styrene copolymer blends, poly(meth)acrylate-polyvinylidene difluoride blends, styrene copolymers and polysulfones and mixtures thereof.

Particularly preferred polymers are transparent or at least translucent. Examples include: polypropylene, polyvinylbutyral, nylon-[6], nylon-[6,6], polycarbonate, polycarbonate-polyethylene terephthalate blends, polycarbonate-polybutylene terephthalate blends, polycarbonate-acrylonitrile/styrene/acrylonitrile copolymer blends, polycarbonate-acrylonitrile/butadiene/styrene copolymer blends, polymethyl methacrylate-acrylonitrile/butadiene/styrene copolymer blends (MABS), polyethylene terephthalate, polybutylene terephthalate, polymethyl methacrylate, impact-modified polymethyl methacrylate, polybutyl acrylate, polymethyl methacrylate-polyvinylidene difluoride blends, acrylonitrile/butadiene/styrene copolymers (ABS), styrene/acrylonitrile copolymers (SAN), polyphenylenesulfone and mixtures comprising 2 or more (e.g. 2, 3, 4, 5) of the afore-mentioned polymers.

Suitable polymer preparations for laser welding comprise

A) a thermoplastic matrix polymer suitable for forming the plastics parts,

B) at least one compound of the general formula (I) as defined before,

C) optionally at least one further additive.

Those polymer preparations for laser welding are likewise in accordance with the invention and are suitable for producing fusion-bonded plastics parts with the aid of laser radiation whose wavelength is outside the visible region.

Polymer preparations for laser welding may advantageously be produced by a conventional extrusion or kneading process. The components B), and, if present, C) may be mixed from the outset, in the weight ratio corresponding to the desired end concentration, with the matrix polymer A) (direct compounding), or a distinctly higher concentration of B) and, if present, C) may initially be selected and the concentrate formed (masterbatch) subsequently diluted with further matrix polymer A) in the course of the manufacture of the parts to be fused.

Suitable additives C) are UV stabilizers, antioxidants, processing plasticizers, etc.

In addition, the polymer preparations for laser welding may comprise at least one colorant for establishing a desired hue as additive, especially transparent organic pigments and in particular dyes, for example C.I. Pigment Yellow 138, 139, 147, 183, 185 192 and 196, C.I. Pigment Orange 70, C.I. Pigment Red 149, 178 and 179, 181, 263, C.I. Pigment Violet 19 and 29, C.I. Pigment Blue 15, 15:1, 15:3 and 15:4, C.I. Pigment Green 7 and 36, C.I. Solvent Yellow 14, 21, 93, 130, 133, 145, 163, C.I. Solvent Red 52, 135, 195, 213, 214 and 225, C.I. Solvent Blue 35, 45, 67, 68, 97, 104, 122, 132, C.I. Solvent Violet 13, 46, 49, C.I. Solvent Green 3, 5 and 28, C.I. Solvent Orange 47, 60, 86, 114, and 163, C.I. Solvent Brown 35, 53, and also C.I. Disperse Yellow 54, 87, 201, C.I. Disperse Orange 30, C.I. Disperse Red 60 and C.I. Disperse Violet 57

A further possible additive group is that of additives which likewise modify the visual appearance, the mechanical properties or else the tactile properties, for example matting agents, such as titanium dioxide, chalk, barium sulfate, zinc sulfide, fillers, such as nanoparticulate silicon dioxide, aluminium hydroxide, clay and other sheet silicates, glass fibers and glass spheres.

The following examples illustrate the invention without restricting it.

EXAMPLES

Example 1

Preparation of

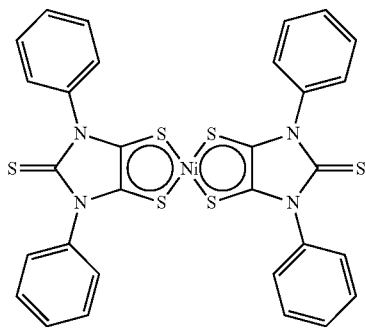

The compound is known from Eur. J. Inorg. Chem. 2003, 1939-1947 and its preparation is described therein.

1,3-diphenyl-4,5-dioxo-imidazoline is reacted under reflux with metallic nickel and Lawesson's reagent in toluene. Using chlorobenzene instead of toluene leads to a higher yield. Absorption maximum (chloroform): 1023 nm

Example 2

Preparation of

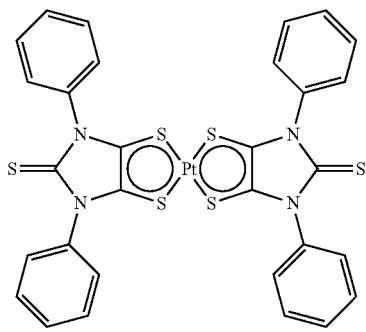

Reaction is carried out analogously to Example 1, with platinum dichloride and Lawesson's reagent. Absorption maximum (chloroform): 1022 nm

Example 3a

Preparation of

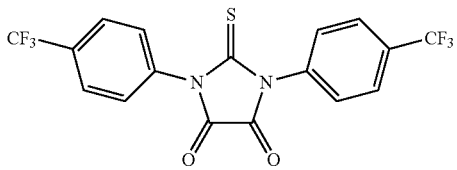 [SMILES: O=C1C(=O)N(c2ccc(C(F)(F)F)cc2)C(=S)N1c1ccc(C(F)(F)F)cc1]

2.0 parts of 1,3-di-(4-trifluoromethyl)phenyl-thiourea are dissolved in 130 parts of dichloromethane at 22° C. Over a period of 20 minutes 0.99 parts of oxalyl chloride are added at 22 to 25° C. to the stirred solution. After a further hour of stirring the solution is evaporated at 40° C. to dryness. 1.7 parts of the product are obtained (lit. Bioorganic Chemistry 17 (2009), 1437-1444).

Example 3b

Preparation of

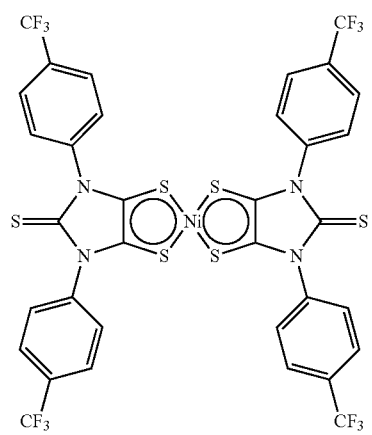

1.70 parts of the product from Example 3a, 0.115 parts of metallic nickel and 1.70 parts of Lawesson's reagent are heated to 130° C. under nitrogen in 130 parts of chlorobenzene. After 120 minutes reaction time the solution is cooled down to 25° C. and the precipitation is filtered off, washed with water and some acetone. The absorption maximum of the product is found at 1018 nm (chloroform).

Example 4a

Preparation of

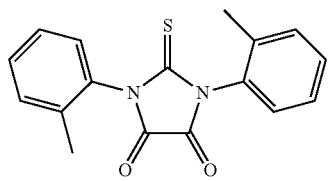 [SMILES: Cc1ccccc1N1C(=O)C(=O)N(c2ccccc2C)C1=S]

10.46 parts of 1,3-Di(o-tolyl)thiourea are dissolved in 300 parts of dichloromethane at 25° C. Over a period of 20 minutes 5.29 parts of oxalyl chloride are added at 25° C. to the stirred solution. After a further hour of stirring at 25° C. the solution is evaporated at 60° C. to dryness: 13.3 parts of N,N'-Di-(o-tolyl)-2-imino-1,3-thiazolidin-4,5-dione are obtained which are added to 400 ml methanol. The mixture is heated to 65° C. for 10 minutes. The solution is cooled down to 25° C. and the precipitate is filtered off, washed with methanol and dried at 50° C. in vacuo: 5.3 g product

Example 4b

Preparation of

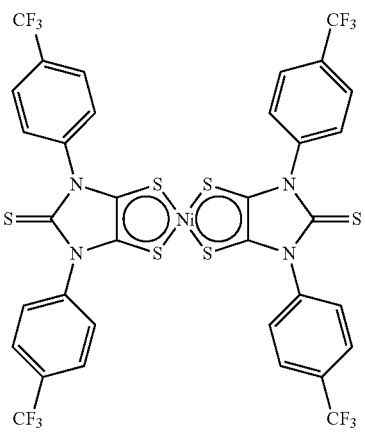

3.79 parts of the product from Example 4a, 0.35 parts of metallic nickel and 5.1 parts of Lawesson's reagent are heated to 130° C. under nitrogen in 450 parts of chlorobenzene.

After 120 minutes reaction time the solution is cooled down to −10° C. and the precipitate is filtered off, washed with ethanol and some acetone. Recrystallization from chlorobenzene yields black crystals. The absorption maximum of the product is found at 1010 nm (chloroform).

Example 5a

Preparation of

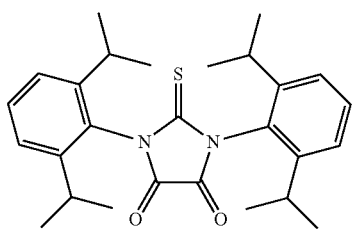 [SMILES: CC(C)c1cccc(C(C)C)c1N1C(=O)C(=O)N(c2c(C(C)C)cccc2C(C)C)C1=S]

10.0 parts of 1,3-Di(2,6-diisopropylphenyl)thiourea are dissolved in 220 parts of dichloromethane at 20° C. Over a period of 5 minutes 3.33 parts of oxalyl chloride are added at 21° C. to the stirred solution. After a further hour of stirring at 21° C. the solution is evaporated at 60° C. to dryness: 12.1 parts solid are obtained, which are added to 400 ml methanol. The mixture is heated to 65° C. for 10 minutes. The solution is filtered and cooled down to 25° C. The precipitate is filtered off, washed with methanol and dried at 50° C. in vacuum (drying oven): 9.9 g yellow product (Fp. 211-212° C.).

Example 5b

Preparation of

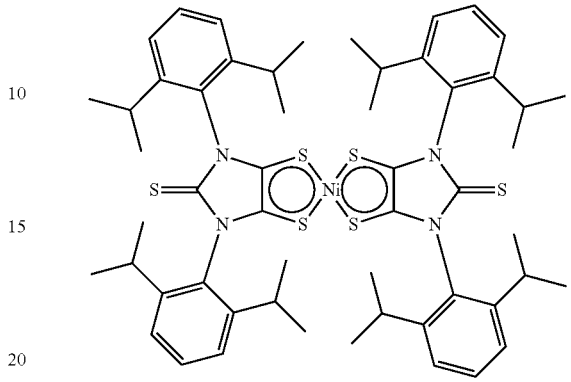

2.07 parts of the product from Example 5a, 0.13 parts of metallic nickel and 1.96 parts of Lawesson's reagent are heated to 132° C. under nitrogen in 150 parts of chlorobenzene. After 180 minutes reaction time the dark solution is cooled down and evaporated to dryness at 50° C. For purification the crude product is recrystallized twice from butylacetate. Dark brown crystals are collected by filtration. The absorption maximum of the product is found at 1020 nm (tetrahydrofurane).

Application Examples

Example A1

Printing 11.9 parts of vinyl chloride, 2.1 parts of vinyl acetate, 10 parts of ethoxypropanol, 75.5 parts of methyl ethyl ketone and 1.0 parts of the product from Example 1 are shaken together with 150 g of glass beads for 30 minutes in a Skandex mixer. The resulting printing ink is applied to contrast paper using a doctor blade (film thickness when damp: 6 μm). The print is visually colorless, but is clearly visible in the IR range using an IR-viewing device (cut-off filter 715 nm). The fastness to light, chemical agents and solvents is excellent.

Example A2

Printing

By proceeding as indicated in Example A1, but using the IR absorber from Example 5b, there accordingly is likewise obtained a colorless print having excellent fastness to light which is clearly visible in the infrared range using an IR-viewing device. Resistance against chemicals and solvents is excellent too.

Example A3

Printing

An offset ink absorbing IR radiation is prepared containing 2.5 weight percent on solids of the compound from example 1. The ink is prepared on a 3-roll mill and comprises 10 weight percent of high tack varnish (CAS 68458-35-5, alkyd resin), 86.5 weight percent of a commercial offset varnish and 1 weight percent of a drying agent (based on CAS 136-52-7; cobalt bis(2-ethylhexanoate) and oleic acid, CAS 112-80-1). The ink is printed by an offset printing equipment to banknote paper. The print is visually almost colorless, but is clearly visible in the IR range using an IR-viewing device (cut-off filter 715 nm). The print exhibits excellent light fastness and very good resistance against all types of solvents, acids, bases, hydrogen peroxide, hypochlorite, sodium sulfite, boiling water etc.

Example A4

Printing

By proceeding as indicated in Example A3, but using 3.7 weight percent on solids (corrected for molecular weight relation) IR absorber from Example 5b, there accordingly is likewise obtained a colorless offset print having excellent fastness to light which is clearly visible in the infrared range using an IR-viewing device. Resistance against all types of solvents, acids, bases, hydrogen peroxide, hypochlorite, sodium sulfite, boiling water etc. is good.

Comparative Example

Printing

By proceeding as indicated in Example A3, but using 2 weight percent on solids (corrected for molecular weight relation) IR absorber from Example 1 of WO 2008/086931 with the structure indicated below there accordingly is likewise obtained a colorless offset print having excellent fastness to light which is clearly visible in the infrared range using an IR-viewing device.

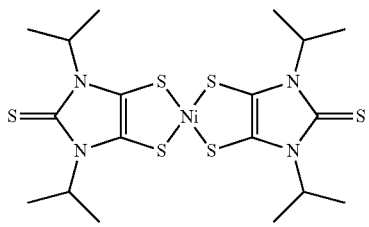

Resistance against solvents like ethanol, white spirit, acids, bases, hydrogen peroxide synthetic sweat and detergents is excellent. But resistance against solvents like toluene, acetone, boiling water or against aggressive chemicals like hypochlorite is not sufficient for banknote printing.

For testing procedure cf. "Chemical and Physical Resistance" in "Extract of the ANNEX 13 of the Technical Specification for Euro banknote production" (European Central Bank; July 2004).

In the following table the test results of the critical fastnesses are given for Example A3, A4 and the present comparative example.

| Resistance against: | Example A3 | Example A4 | Comparative Example |
|---|---|---|---|
| Acetone | 4 | 3 | 2 |
| Toluene | 4 | 3-4 | 2 |
| Hypochlorite (5%) | 4 | 3-4 | 1 |
| Boiling Water | 3-4 | 3 | 1-2 |

Evaluation by IR camera with cut-off filter (715 nm)
Ranking list according to the European Central Bank
4: no change or minor changes not visible with naked eyes
3: minor change
2: considerable change; less than 50% damaged
1: major change; more than 50% damaged
0: element disappeared Example A5

Laser-Welding of Plastics

Using an injection-molding machine, the IR absorber from Example 1 is incorporated into a polycarbonate disc having a thickness of 2 mm (concentration: 100 ppm). Using an Nd:YAG laser, the resulting, virtually colorless disc is welded at a power of 30 watt and a rate of advance of 20 mm/s to a second 1 mm-thick pure polycarbonate disc not containing IR absorber. The resulting weld is characterized by an excellent bond, unchanged transparency, no melt irruptions and no bubbling. Under heavy mechanical loading, breakage of the discs does not occur at the welded seam.

Example A6

Laser-Welding of Plastics

By proceeding as indicated in Example A5, but using the IR absorber from Example 5b, a virtually colorless polycarbonate disc is likewise obtained which has excellent welding properties. The resulting weld has unchanged transparency, the welding leaves no melt irruptions or bubbling and the strength of the weld is excellent.

Examples A7 and A8

By proceeding as indicated in Examples A5 and A6, but, instead of using an Nd:YAG laser (1064 nm), using a diode laser having an emission wavelength of 980 nm, similarly good results to those described in Examples A5 and A6 are obtained.

Examples A9 and A10

By proceeding as indicated in Examples A5 and A6, but, instead of using an Nd:YAG laser (1064 nm), using a diode laser having an emission wavelength of 940 nm, a comparably good weld is obtained at a laser power of 80 watt.

Example A11

By proceeding as indicated in Example A5, but using polypropylene discs having a thickness of 1.5 mm, the welds obtained are likewise very good.

The invention claimed is:
1. A security printing method comprising contacting a printing ink formulation comprising a colorless IR absorber with a substrate to produce a printed security document,
wherein said colorless IR absorber is a compound of formula (I)

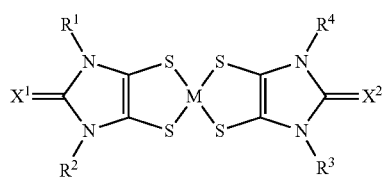
(I)

wherein

M is Ni, Pd, or Pt, $X^1$ and $X^2$ are each independently sulfur or oxygen, $R^1$, $R^2$, $R^3$, and $R^4$ are each independently selected from the group consisting of unsubstituted aryl, substituted aryl, unsubstituted heteroaryl, and substituted heteroaryl.

2. The method according to claim 1, wherein M is Ni.

3. The method according to claim 1, wherein the compound is of formula (1) is at least one compound selected from the group consisting of compounds of formulae (1) to (37):

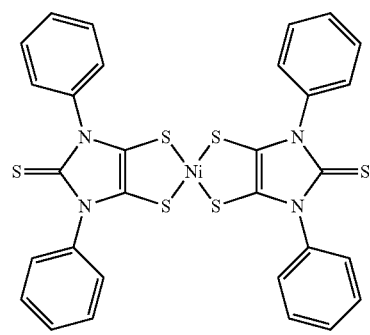
(1)

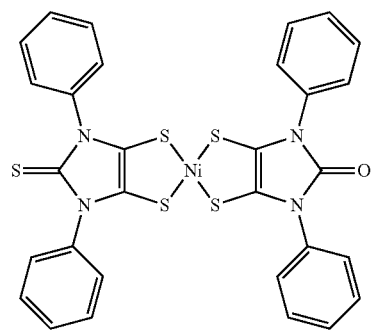
(2)

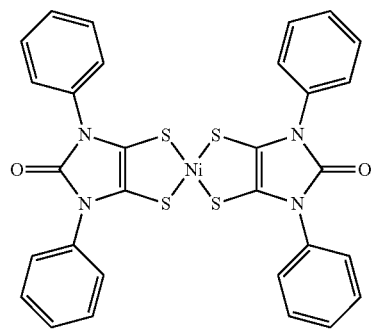
(3)

-continued

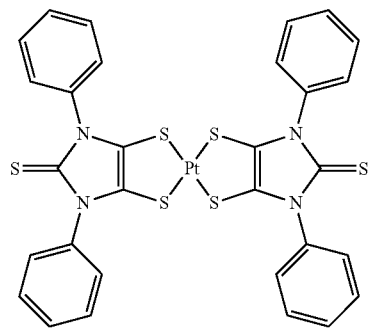
(4)

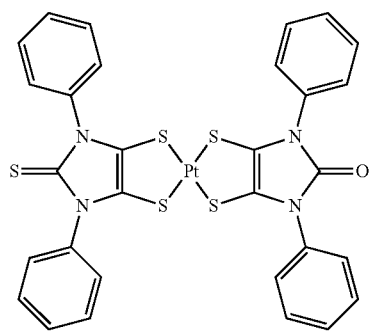
(5)

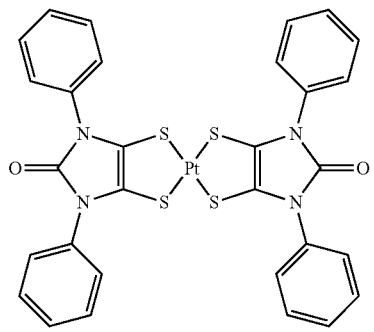
(6)

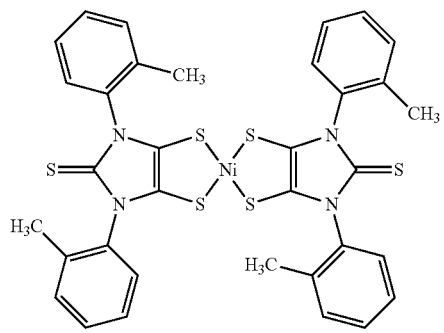
(7)

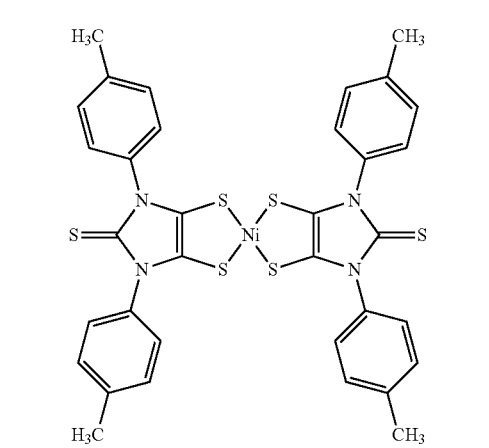
(8)
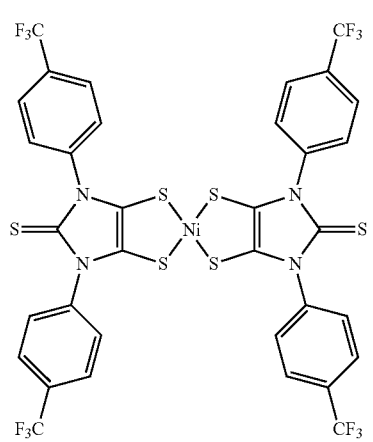
(12)
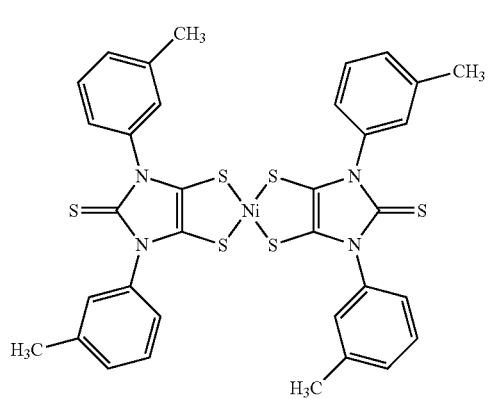
(9)
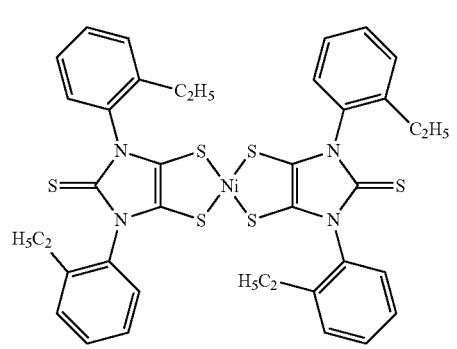
(13)
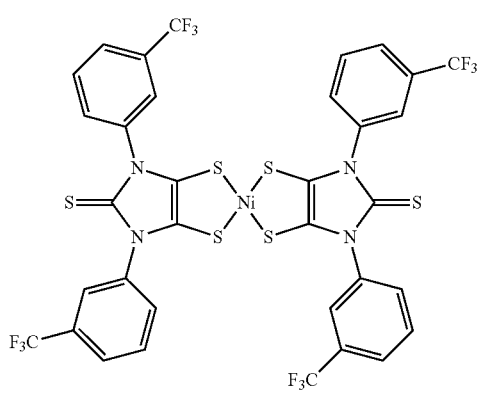
(10)
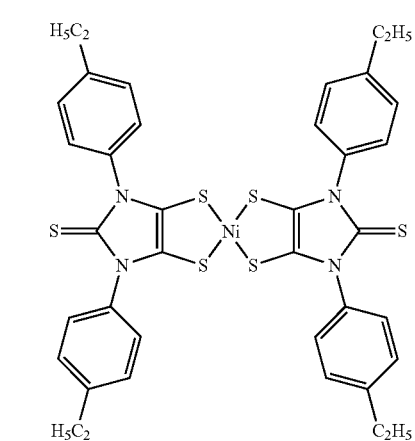
(14)
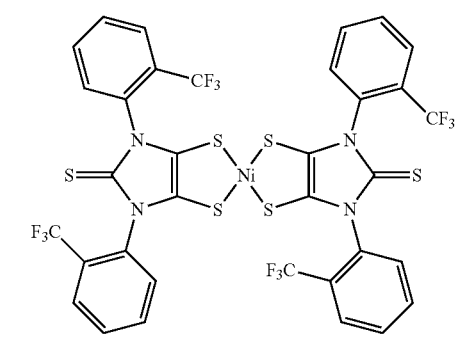
(11)
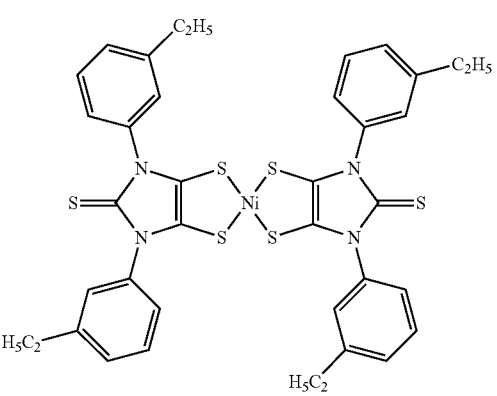
(15)

-continued
(16)
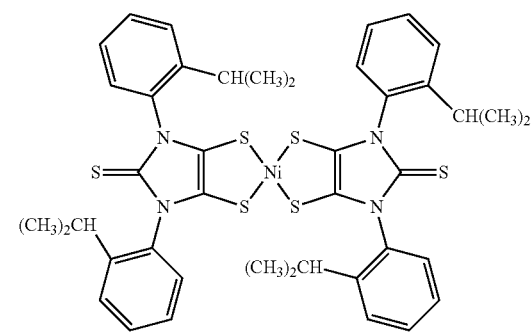
(17)
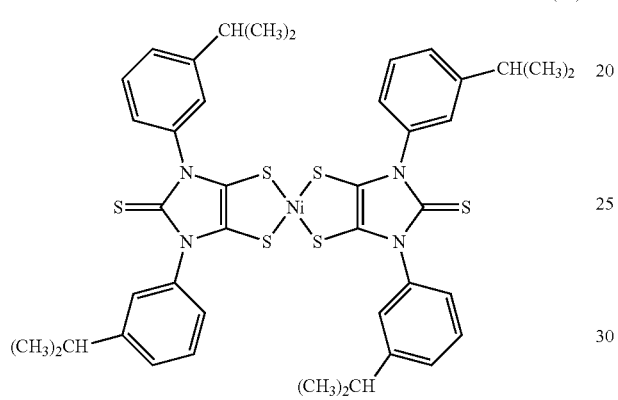
(18)
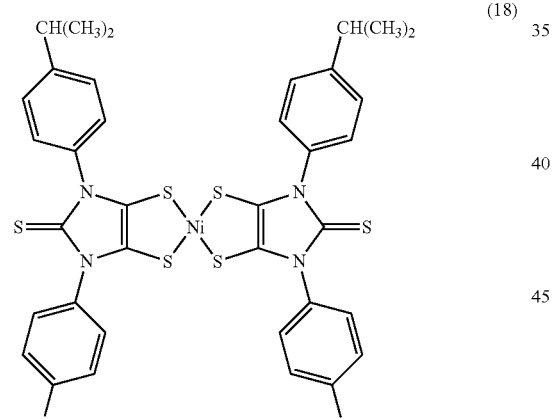
(19)
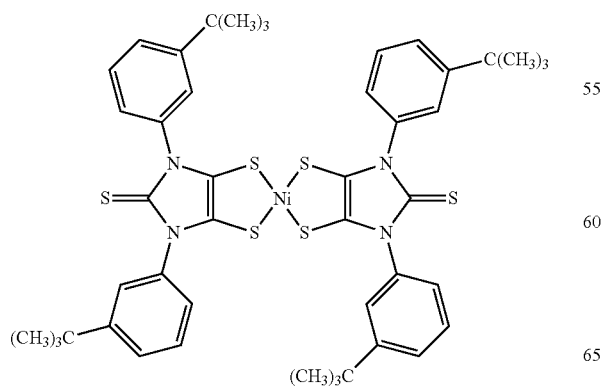
-continued
(20)
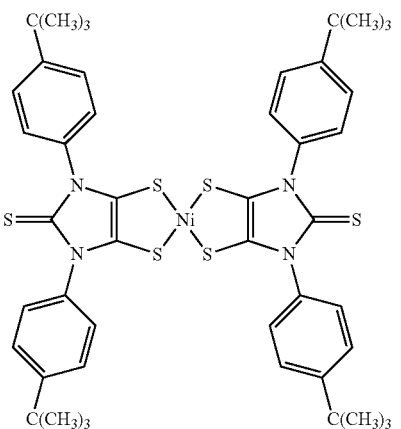
(21)
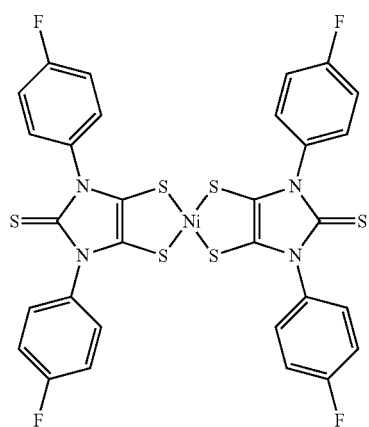
(22)
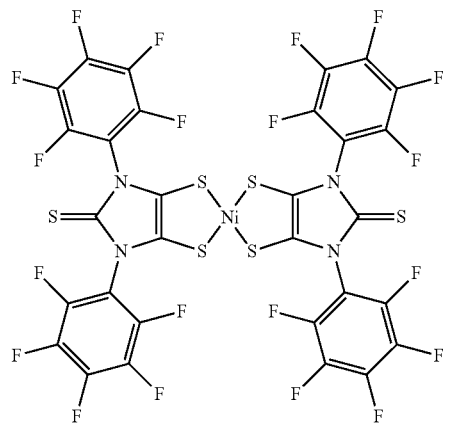
(23)
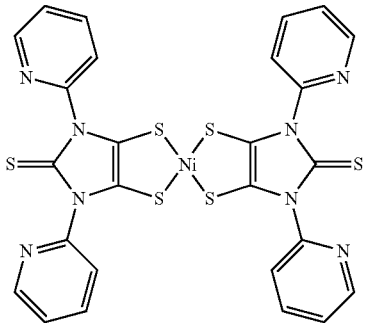

(24) 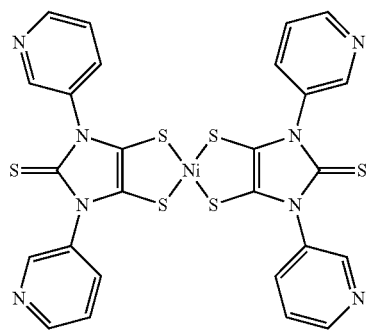
(25) 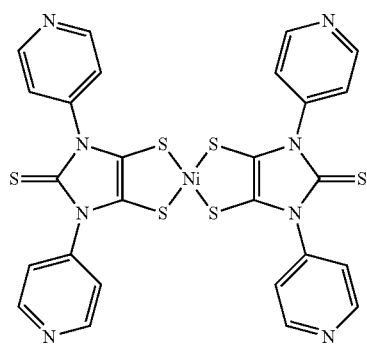
(26) 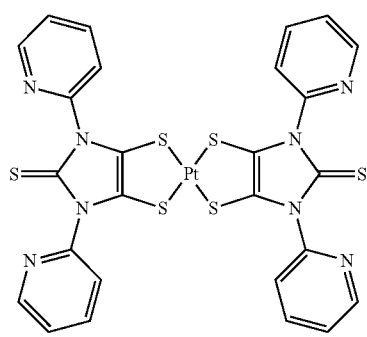
(27) 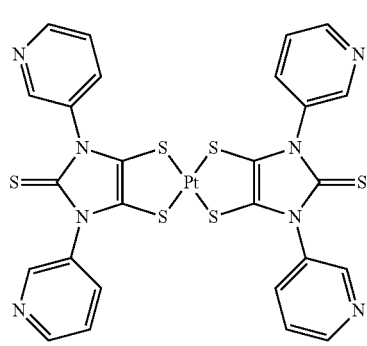
(28) 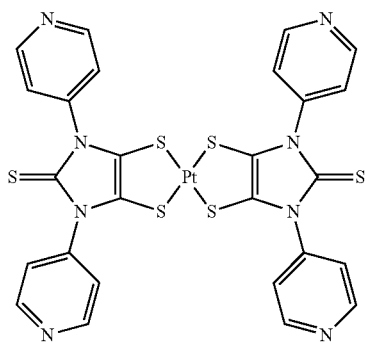
(29) 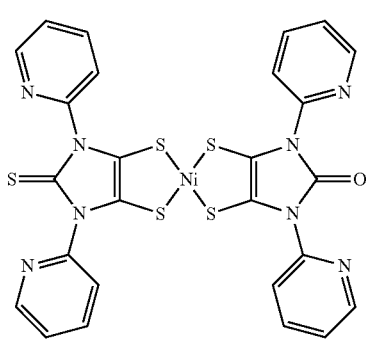
(30) 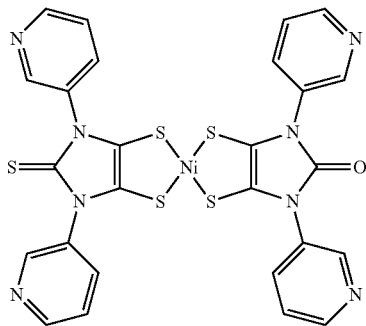
(31) 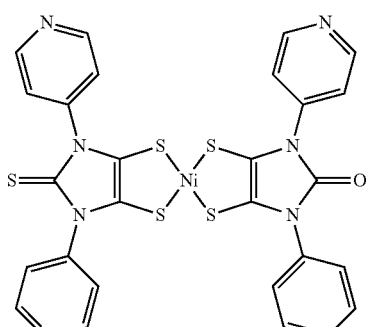

(32)

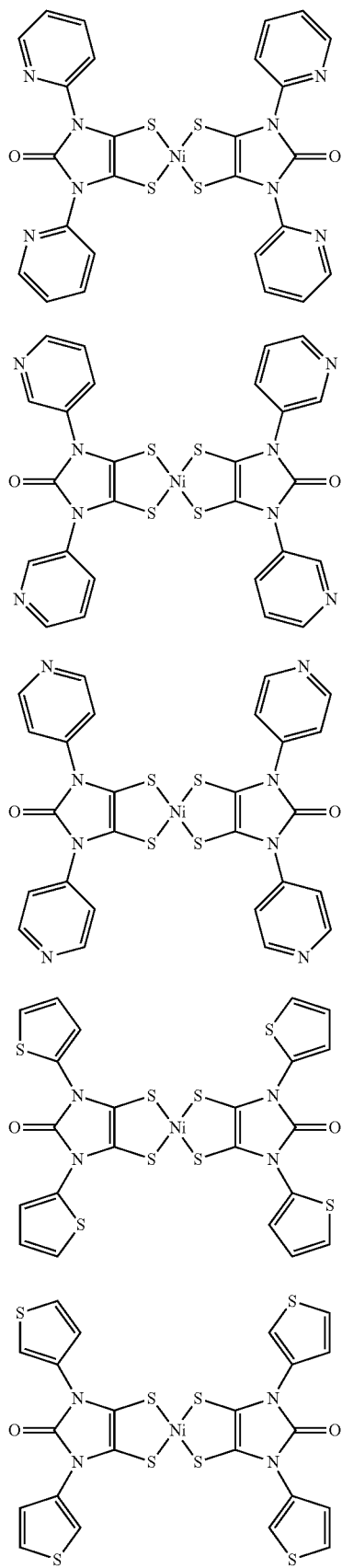

(33)

(34)

(35)

(36)

(37)

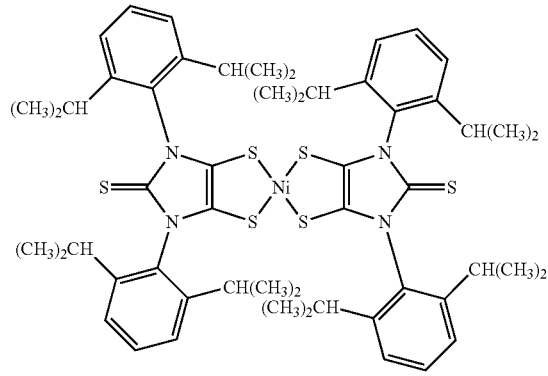

4. The method according to claim 1, wherein the compound is in a form of a mixture, the mixture comprising the compound of formula (I) and a further IR absorber different from a compound of formula (I).

5. The method according to claim 1, wherein the printed security document is a bank note.

6. The method according to claim 1, wherein the contacting improves fastness properties of the printed security document.

7. A printing ink formulation, comprising
a) a compound of formula (I):

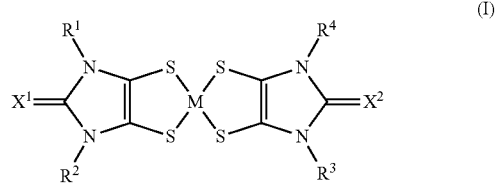

wherein
M is Ni, Pd, or Pt,
$X^1$ and $X^2$ are each independently sulfur or oxygen,
$R^1$, $R^2$, $R^3$, and $R^4$ are each independently selected from the group consisting of unsubstituted aryl, substituted aryl, unsubstituted heteroaryl, and substituted heteroaryl, and wherein the compound is a colourless IR absorber,
a polymeric binder,
a solvent,
optionally a colorant, and
optionally a further additive.

8. The printing ink formulation according to claim 7, comprising
0.0001 to 25% by weight of the compound of formula (I),
5 to 74% by weight of the polymeric binder,
1 to 94.9999% by weight of the solvent,
0 to 25% by weight of the colorant, and
0 to 25% by weight of the additive,
wherein a sum of the weights of the compound, the polymeric binder, the solvent, the colorant, and the additive is 100%.

9. A security document, wherein the security document is obtained by a printing method, according to claim 1.

10. The security document according to claim 9, wherein the security document is at least one selected from the group consisting of a bank note, a passport, a check, a voucher, an ID-card, a transaction card, a stamp and a tax label.

11. The method according to claim 1, wherein $X^1$ is oxygen.

12. The method according to claim 3, wherein said compound is at least one compound selected from the group consisting of formula (1) and (37).

13. A printing ink formulation, comprising:
   at least one compound selected from the group consisting of formula (1) to (37) according to claim 3,
   a polymeric binder,
   a solvent,
   optionally a colorant, and
   optionally a further additive.

14. The printing ink formulation according to claim 13, comprising
   0.0001 to 25% by weight of at least one compound selected from the group consisting of formula (1) to (37),
   5 to 74% by weight of the polymeric binder,
   1 to 94.9999% by weight of the solvent,
   0 to 25% by weight of the colorant, and
   0 to 25% by weight of the additive,
   wherein a sum of the weights of the compound, the polymeric binder, the solvent, the colorant, and the additive is 100%.

* * * * *